(12) United States Patent
Aoki et al.

(10) Patent No.: US 6,751,289 B2
(45) Date of Patent: Jun. 15, 2004

(54) X-RAY DIAGNOSTIC APPARATUS

(75) Inventors: Kunio Aoki, Yaita (JP); Michitaka Honda, Yaita (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 09/971,591

(22) Filed: Oct. 9, 2001

(65) Prior Publication Data

US 2002/0064254 A1 May 30, 2002

(30) Foreign Application Priority Data

Oct. 10, 2000 (JP) .................................... 2000-308965

(51) Int. Cl.[7] ................................................ H05G 1/64
(52) U.S. Cl. ................. 378/98.7; 378/98.11; 378/98.12
(58) Field of Search ............................. 378/98.7, 98.8, 378/98.11, 98.12, 207; 250/370.08, 370.09

(56) References Cited

U.S. PATENT DOCUMENTS

| | | | | |
|---|---|---|---|---|
| 5,452,338 A | * | 9/1995 | Granfors et al. | 378/98.11 |
| 5,530,238 A | * | 6/1996 | Meulenbrugge et al. | 250/208.1 |
| 6,028,913 A | * | 2/2000 | Meulenbrugge et al. | 378/98.8 |
| 6,246,746 B1 | * | 6/2001 | Conrads et al. | 378/98.7 |
| 6,353,654 B1 | * | 3/2002 | Granfors et al. | 378/19 |

\* cited by examiner

*Primary Examiner*—David V. Bruce
*Assistant Examiner*—Courtney Thomas
(74) *Attorney, Agent, or Firm*—Oblon, Spivak, McClelland, Maier & Neustadt, P.C.

(57) ABSTRACT

When X-ray irradiation is performed with many X doses and the fall of temporary sensibility or the rise of the temporary offset arises, it is the X-ray diagnostic equipment which computes the correction by sensitiveness multiplier based on the sensibility characteristic or offset characteristic of each pixel, and rectifies data. In this X-ray diagnostic equipment, the correction by sensitiveness multiplier for data correction is determined based on the signal value detected last time at least. In integrating this correction by sensitiveness value from each pixel to the output signal, the influence by the fall of temporary sensibility or the rise of the temporary offset is removed.

17 Claims, 9 Drawing Sheets

| t | Electron number occurred in one pixel | Trap occurring probability | Trap number | Electron number to be output from one pixel of detection film | Sensitivity |
|---|---|---|---|---|---|
| 0 | $X_0$ | $P_0$ | $Y_0 = M_0 P_0$ | $Z_0 = X_0(1-Y_0/N)$ | $(1-Y_0/N)$ |
| 1 | $X_1$ | $P_1$ | $Y_1 = M_0 P_1 + M_0 P_0 (1-P_1) A$ $= M_0 P_1 + (1-P_1) Y_0 A$ | $Z_1 = X_1(1-Y_1/N)$ | $(1-Y_1/N)$ |
| 2 | $X_2$ | $P_2$ | $Y_2 = M_0 P_2 + (1-P_2) Y_1 A$ | $Z_2 = X_2(1-Y_2/N)$ | $(1-Y_2/N)$ |
|   |   |   |   |   |   |
| i | $X_i$ | $P_i$ | $Y_i = M_0 P_i + (1-P_i) Y_{i-1} A$ | $Z_i = X_i(1-Y_i/N)$ | $(1-Y_i/N)$ |

FIG. 6

X-RAY DIAGNOSTIC APPARATUS

CROSS-REFERENCE TO RELATED APPLICATIONS

This application is based upon and claims the benefit of priority from the prior Japanese Patent Application No. 2000-308965, filed Oct. 10, 2000, the entire contents of which are incorporated herein by reference.

BACKGROUND OF THE INVENTION

1. Field of the Invention

The present invention relates to X-ray diagnostic apparatus which can correct a signal output by the X-ray detector.

2. Description of the Related Art

Heretofore, an X-ray photofluorographic imaging apparatus provided with an image intensifier (I.I.)-TV camera system has been used as X-ray imaging means. The I.I., as its schematic sectional view is shown in FIG. 1, comprises: an input fluorescent plane that converts an incident X-ray into an image of visible radiation; a photoelectric conversion film that converts the light intensity distribution of the visible radiation image and to which cathode potential is given; an anode to which an accelerated field accelerating electron beams irradiated from the photoelectric conversion film is given; focusing electrode that focuses the electron beams on the output fluorescent plane; and the output fluorescent plane to which the accelerated electron beams are made incident and converted into an optical image again. Then, the optical image formed on the output fluorescent plane is amplified to a luminance a few thousand times as the optical image on the input fluorescent plane. The image whose luminance has been amplified is projected on a monitor unit through the TV camera or stored in an image storage unit.

In recent years, on the other hand, an X-ray detector in which a semiconductor is used in an X-ray detection part has been proposed from a viewpoint of manufacturing a small and thin detector.

As the configuration of the X-ray detector using the semiconductor, an indirect conversion type X-ray detector (U.S. Pat. No. 4,689,487) and a direct conversion type X-ray detector (U.S. Pat. No. 5,319,206) and the like are proposed.

The indirect conversion type X-ray detector converts the X-ray into light via a chemical such as cesium iodide (CsI) crystal, converts the light intensity into electric charge by the photoelectric conversion operation of a photodiode, and stores the electric charge in a capacitance for every pixel. Then, switching means such as a thin film transistor (hereinafter, abbreviated as TFT) matrix sequentially reads out the accumulated electric charge, a charge amplifier (also called an initial step integrating amplifier) converts it into a voltage, and the voltage is subject to an A/D conversion to obtain a digital image signal.

On the other hand, as shown in the schematic sectional view of FIG. 2A, in the direct conversion type X-ray detector, the X-ray made incident to the semiconductor such as selenium (Se) under high field contributes to occurring of the electric charge due to a direct photoelectric effect, and thus the electric charge is accumulated in a signal accumulation capacitance for every pixel. Then, similarly to the direct conversion type X-ray detector, the accumulated electric charge is sequentially read out by the switching of the TFT, converted into the voltage by the charge amplifier (not shown), and the voltage is subject to the A/D conversion to obtain the digital image signal.

Furthermore, when diagnosis is performed using the foregoing X-ray detector, the sensitivity of a plurality of detection devices provided in the X-ray detector has dispersion. Therefore, a sensitivity correction table 103 and an offset correction table 102 have been conventionally used as shown in a block diagram of FIG. 2B in order to correct the sensitivity.

Namely, the sensitivity correction table 103 is the one where a sensitivity characteristic in the X-ray detector is measured in advance and different sensitivity correction coefficient for every pixel (for every detected device) is stored. The sensitivity correction table 103 outputs a detection value which is corrected by multiplying the coefficient by the output of the X-ray detector. In addition, the offset correction table 102 is the one where an offset characteristic in the X-ray detector is measured in advance and different offset correction coefficient for every pixel is stored. The offset correction table 102 outputs a detection value which is corrected by subtracting the coefficient from the output of the X-ray detector 101.

However, the inventors found out a phenomenon that the sensitivity temporarily reduces and the offset increases in accordance with the intensity of the X-ray when the X-ray having intensity of a predetermined value or more is made incident, in the X-ray detector, among others, the X-ray detector using the semiconductor. In other words, this means that the sensitivity or the offset changes with time in each pixel.

This phenomenon is conspicuous when the conditions of the X-ray intensity, that is, an X-ray quantity being a product between an X-ray tube current and exposure time, are greatly different. For example, in a fluorography where relatively light X-ray is continuously irradiated, the phenomenon appears remarkably when a time of X-ray exposure is relatively long, and in an imaging where relatively strong X-ray is intermittently irradiated, the phenomenon appears remarkably when strong X-ray exposure is irradiated. It is to be noted that there is a case where a few hundred times of difference of a maximum electric charge accumulated in one pixel between the fluorography and the imaging.

The decrease of this temporary sensibility and the increase of the offset causes superimposing the after-image which is based on the X rays detected the last time and called ghost on the regular image acquired by fluorography or imaging.

BRIEF SUMMARY OF THE INVENTION

Therefore, the object of the present invention is to solve the foregoing problems, and to provide an X-ray diagnostic apparatus and a control method thereof configured to acquire an image by properly correcting the output of the X-ray detector even when the temporary reduction of the sensitivity (hereinafter, may be referred as the sensitivity) or increase of the offset occurs.

According to an aspect of the present invention there is provided an X-ray diagnostic apparatus comprises: a detector configured to detect an incident X-ray; an operator configured to estimate a characteristic change of the X-ray detector based on a value of a signal previously detected the detector at least last time; and a first correction device configured to execute a correction by which the estimated characteristic change is cancelled to a signal output from the X-ray detector.

According to the second aspect of the present invention there is provided an X-ray diagnostic apparatus comprises: a X-ray detector having a plurality of semiconductor elements arranged in the shape of a 2-dimensional matrix and configured to detect an incident X-ray and generate electric information; an operator configured to estimate a characteristic change of each of the semiconductor elements based on a value of a signal previously detected by each of the plurality of the semiconductor elements at least last time; and a correction device configured to execute a correction by which each of the estimated characteristic change is cancelled to each of the signals output from each of the plurality of the semiconductor elements.

According to the third aspect of the present invention there is provided an X-ray diagnostic apparatus comprises: a X-ray detector having a plurality of semiconductor elements arranged in the shape of a 2-dimensional matrix and configured to detect an incident X-ray and generate electric information; a memory configured to store a correlation relation between an offset characteristic and a sensitivity characteristic of each of the semiconductor elements; a first operator configured to estimate an offset characteristic change of each of the semiconductor elements based on a value of a signal previously detected by each of the plurality of the semiconductor elements at least last time; a second operator configured to estimate a sensitivity characteristic change of each of the semiconductor elements from the estimated offset characteristic change according to the correlation relation; and a correction device configured to execute a correction by which each of the sensitivity characteristic change is cancelled to each of the signals output from each of the plurality of the semiconductor elements.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

FIG. 4 is a block diagram of a data correction unit 21a.

FIG. 6 shows the relation between the electron number occurred in each pixel by executing X-ray irradiation i times in total, a trap occurring probability, the trap number, the electron number to be output and the sensitivity of the detector.

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Next, the first and second embodiments according to the present invention will be described with reference to the drawings.

First Embodiment

Figure 1:
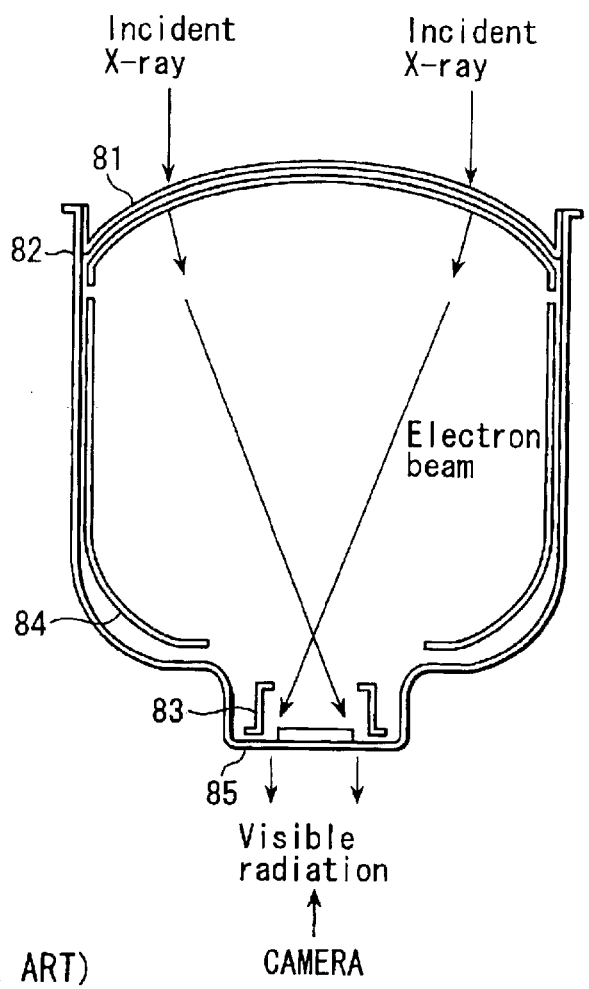
FIG. 1 is a sectional view of the I.I. in a conventional example.
Figure 2B:
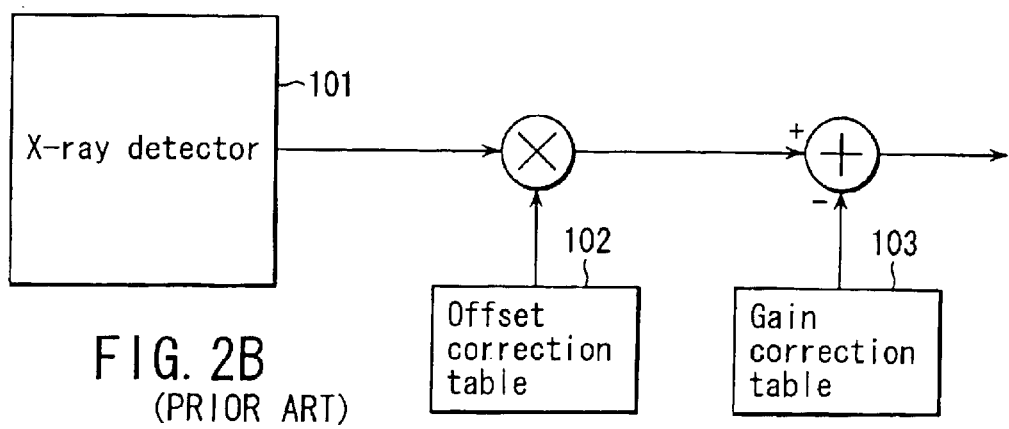
FIG. 2B is a part of a block diagram of the conventional X-ray diagnostic apparatus.
Figure 2A:
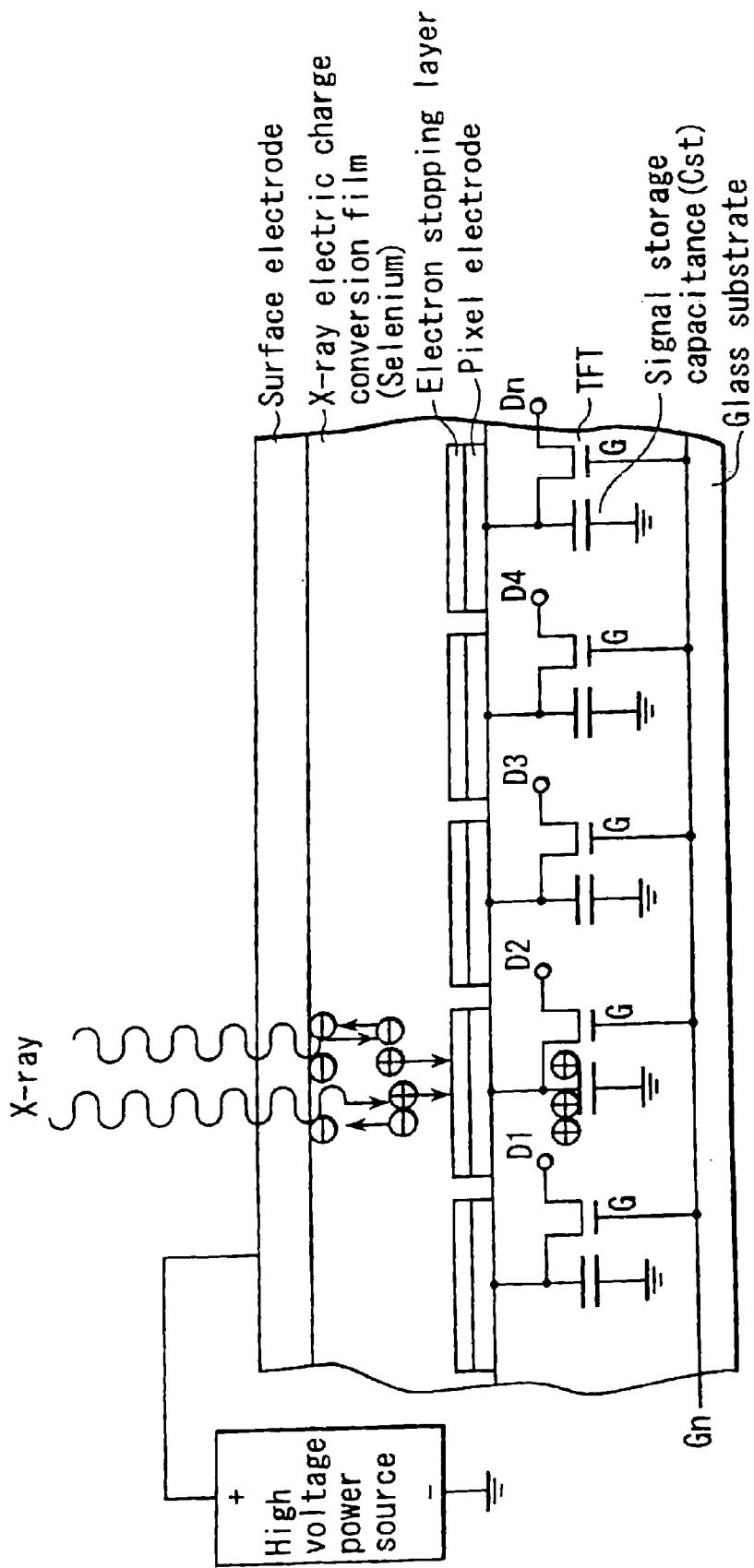
FIG. 2A is a schematic sectional view of the direct conversion type of the conventional X-ray detector.
Figure 3:
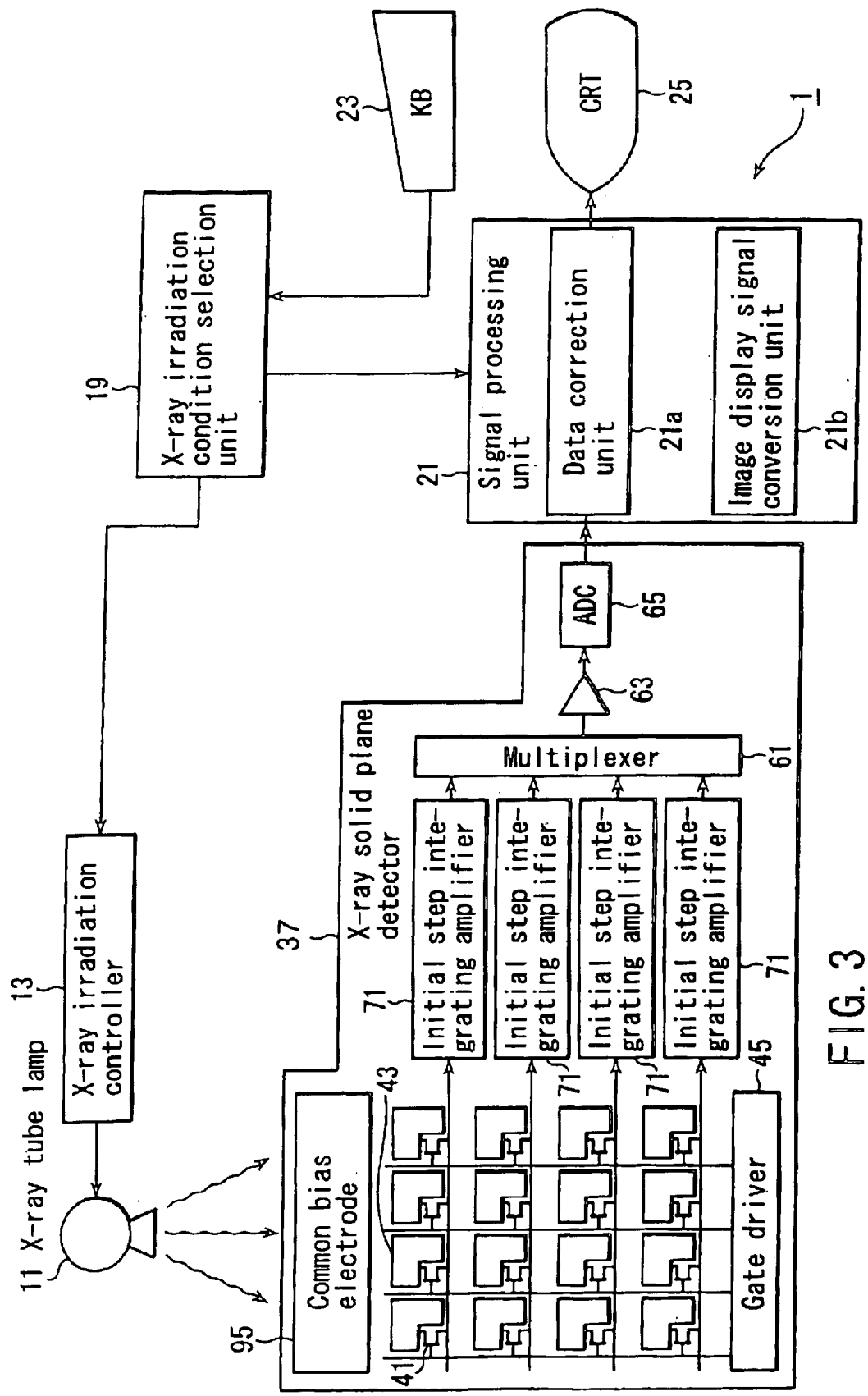
FIG. 3 is a block diagram of the X-ray diagnostic apparatus according to a first embodiment.

FIG. 3 is a block diagram of the X-ray diagnostic apparatus 1 according to the first embodiment. Note that, in general, there are the direct type which changes incidence X-ray into the direct electrical signal, and the indirect type changed into the electrical signal once changing incidence X-ray into the optical signal in the X-ray diagnostic apparatus 1.

To explain the embodiments easily, the X-ray diagnostic apparatus according to the first and second embodiments is taken as the direct type. However, the idea of the present invention is applicable also to indirect type X-ray diagnostic apparatus.

As shown in FIG. 3, the X-ray diagnostic apparatus 1 comprises: an X-ray tube lamp 11 as an X-ray source; an X-ray exposure controller 13 that controls X-ray exposure conditions from the X-ray tube lamp 11; and X-ray exposure conditions selection unit 19; a signal processing unit 21 that corrects X-ray image information to convert into an image display signal; a keyboard 23 (hereinafter, abbreviated as KB) for inputting the X-ray exposure conditions; a CRT to display the X-ray image; and an X-ray solid plane detector 37. It is to be noted that the signal processing unit includes a data correction unit 21a.

The X-ray solid plane detector 37 comprises: a plurality of X-ray conversion devices 43 corresponding to each of the pixels arranged in a matrix state of, for example, 1000× 1000; a plurality of TFTs 41 as a reading switch provided corresponding to each X-ray conversion device 43; a bias electrode 95 that commonly applies a bias voltage to each X-ray conversion device 43; a gate driver 45 that sends a drive signal to gates of the TFTs 41 of each column; a gate driver 45 that sends the drive signal to the gates of the TFTs 41 of each column; initial step integrating amplifiers 71 to which drains of the TFTs 41 of each array are commonly connected; a multiplexer 61 that multiplexes the output of each initial step integrating amplifiers 71 in time-division; an amplifier 63 that amplifies the output of the multiplexer 61; and an analog/digital converter (ADC) 65 that performs analog/digital conversion to the output of the amplifier 63 and to output it to the signal processing unit 21.

It is to be noted that an amorphous-selenium film (hereinafter, abbreviated as an a-Se) is used for the detection film of the X-ray conversion device 43. In addition, the X-ray conversion device 43 may be a direct conversion type X-ray conversion device that converts the X-ray into a direct electric charge, or may be an indirect conversion type X-ray conversion device that converts the X-ray into the visible radiation by a fluorescent material (not shown) formed on the X-ray incident plane and converts the intensity distribution of the visible radiation into the electric charge.

Furthermore, the initial step integrating amplifier 71 is configured to comprise: a differential amplifier; a condenser; and a semiconductor switch such as bilateral gate using, for example, a complementary MOS-FET, in which an opening/closing operation is performed electronically.

The signal processing unit 21 has a data correction unit 21a and an image display signal conversion unit 21b. The data correction unit 21a executes predetermined correction processing to the inputted data in order to remove the influence due to the falling of the sensibility or the rising of the temporary offset of each pixel. The image display signal conversion unit 21b converts the corrected data to image display signals and outputs to the CRT 25.

Figure 4:
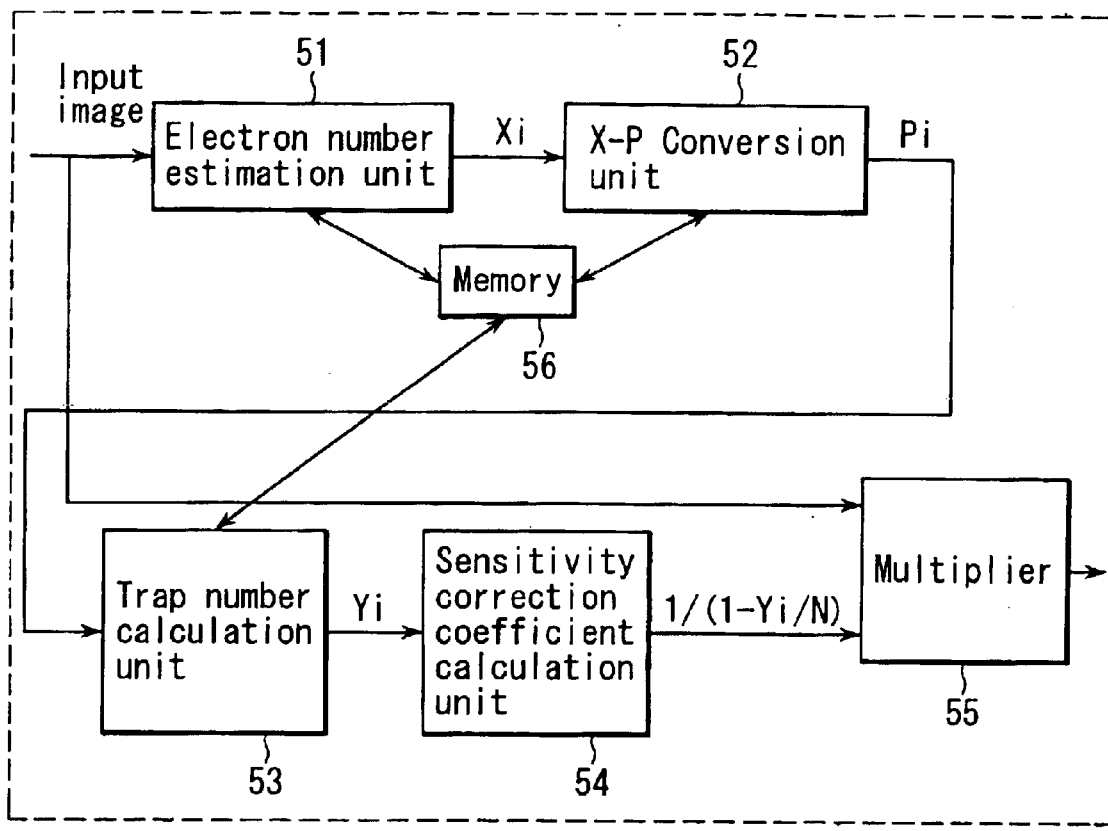

FIG. 4 is the block diagram of the data correction unit 21a. As shown in FIG. 4, the data correction unit 21a comprises an electron number estimation unit 51, an X-P conversion unit 52, a trap number calculation unit 53, a sensitivity correction coefficient calculation unit 54, a multiplier 55 and a memory 56.

The electron number estimation unit 51 estimates the electron number $X_i$ occurred in one pixel based on the output signal of the ADC 65. The estimation is performed according to a collection condition stored in the memory 56. The collection condition is the one showing the relation between the X-ray intensity input to one pixel and the electron number $X_i$ occurred in one pixel. The collection condition can be calculated, for example, from the material of the detection film, a gain factor of the voltage or the like applied to the X-ray conversion device 43. The X-P conversion unit 52 obtains the trap occurring probability $P_i$ of the electronic trap based on the electron number $X_i$ estimated by the electron number estimation unit 51. The trap number calculation unit 53 obtains the trap number Yi based on the trap occurring probability $P_i$ obtained by the X-P conversion unit 52. The sensitivity correction coefficient calculation unit 54 calculates the sensitivity correction coefficient $1/(1-Y_i/N)$ based on the trap number $Y_i$. Here, N means the number of the division ranges of the detection film with a length of one pixel, the number regarded as criteria in order to calculate the sensitivity correction coefficient. The multiplier 55 multiplies the sensitivity correction coefficient $1/(1-Y_i/N)$ with an original image data to output to calculate a corrected data value. The memory 56 stores various parameters used in each processing of the electron number estimation unit 51, the collection conditions used in estimation of the number Xi of the electrons in one pixel and LUT (Look Up Table) used in the trap number Yi calculation processing of the trap in the collection conditions in the X-P conversion unit.

Note that, the configuration of LUT, its example of formation and data correction processing executed by the data correction unit 21a are described in detail later.

It is as follows that an example of series of operations in the diagnosis of the X-ray diagnostic apparatus 1 is described. When performing the X-ray imaging, the fluorography or the like, a menu screen is firstly displayed on the CRT 25, and the X-ray exposure conditions such as a tube voltage, a tube current and the exposure time is input to the X-ray exposure condition selection unit 19 from the KB 23 according to the menu. The X-ray exposure condition selection unit 19 outputs a control signal corresponding to the input X-ray exposure conditions to the X-ray exposure controller 13.

And then, when the X-ray is irradiated from the X-ray tube lamp 11 in accordance with the output of the X-ray exposure controller 13, the intensity of the X-ray that has been made incident to each pixel of the X-ray solid plane detector 37 passing the subject to be analyzed (not shown) is converted into the electric charge by the X-ray conversion device 43, and the electric charge quantity accumulated in each X-ray conversion device 43 is converted into the voltage by the initial step integrating amplifier 71 with the switch of the TFT 41 provided in each pixel.

The output of the initial integrating amplifier 71 is input to the ADC 65 via the multiplexer 61 after amplified by the amplifier 63, written in the signal processing unit 21 after the analog/digital conversion is performed, the data correction and the image display signal are converted, and then the X-ray image is displayed on the CRT 25.

Electronic Trap

Figure 5:
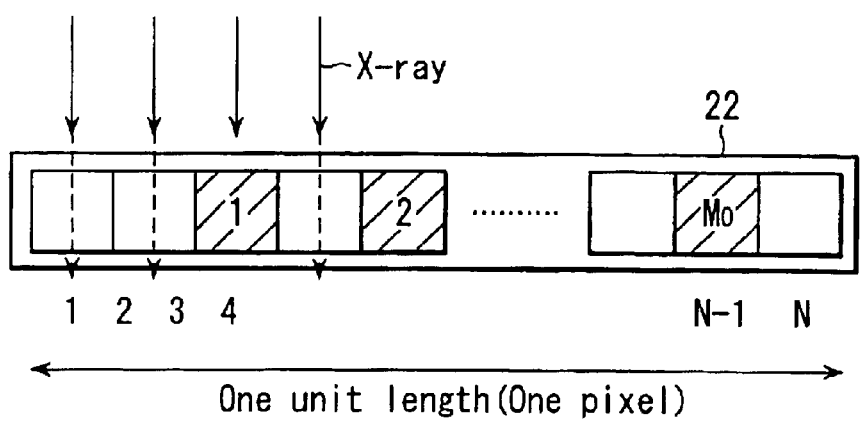
FIG. 5 is a conceptual sectional view of a part of the detection film of the X-ray detector.

Herein, the data correction operation of the signal processing unit 21 will be described in detail. As described, in the X-ray detector, among others, the X-ray detector using the semiconductor, the sensitivity temporarily reduces in accordance with the intensity of the X-ray or causes the phenomenon that the offset increases temporarily when the X-ray of the predetermined value or more is made incident. The influence of an electronic trap is considered to be the cause of this phenomenon. The electronic trap is that the electron (or a positive hole) occurred by external energy such as the X-ray is trapped to an energy level. Referring to FIG. 5, the mechanism that a sensitivity decrease occurs temporarily in the predetermined pixels due to the electronic trap will be quantitatively described below. In order to give concrete explanation, it is supposed that the detector is the direct conversion type.

FIG. 5 is a conceptual sectional view of a part of the detection film of the X-ray detector. Here, in order to explain easily, the sectional view is showing for one pixel. The part of the slash in FIG. 5 is the range from which the trap may be raised (hereafter, referred to as trap possible range), when the detection film with a die length of 1 pixel is divided into N minute ranges. Now, it is supposed that the maximum number of the trap possible ranges is $M_0$. Consequently, the trap should not occur in the region $n-M_0$.

In FIG. 5, the X-ray of certain intensity is irradiated to occur $X_0$ pieces of the electrons (or the holes) in one pixel. There are regions that occur maximum $M_0$ pieces of the traps in one pixel. Suppose that probability that a trap possible range turns to a range in which the trap occurs actually (hereafter, referred to as a trap occurring range) is $P_0$. In this case, the number of all the trap occurring ranges (hereafter, referred to as a trap number) is $M_0P_0$. It is to be noted that the probability $P_0$ that a trap possible range turns to a trap occurring range generally depends on the number of the electrons occurred.

Consequently, when there are $M_0P_0$ pieces of the trap regions, the number of the electrons $Z_0$ output form the detection film is $X_0(1-M_0P_0/N)$.

The trap number $M_0P_0$ should attenuates with time due to any kind of action. The attenuation curve is presumed as $M_t=M_0P_0\exp(-at)$. It is to be noted that $M_t$ is the trap number of the trap number $M_0P_0$ after the time t has passed. Now, supposing there are $M_t$ pieces of the trap regions, there are $M_0-M_t$ pieces of the trap possible regions in which the electronic trap does not occur yet.

After the first X-ray irradiation, the second X-ray having the intensity that generates $X_1$ pieces of the electrons instead of $X_0$ pieces is irradiated. It is presumed that probability to change a trap possible region to a trap generating range is $P_1$ owing to the second X-ray irradiation. In this case, $(M_0-M_t)P_1$ pieces of new trap occurring regions occurs from the trap possible regions in which the electronic trap does not occur yet.

Consequently, When the X-ray having the intensity that occurs $X_1$ pieces of the electrons is irradiated, together with the first X-ray irradiation, $(M_0-M_t)P_1$ pieces of new trap occurring regions exists in total.

In the present embodiment, from the viewpoint of simplifying explanation and practicality, it is supposed that, for example, t is unit time, that is, t=1, and A=exp(−a). In this case, $M_t=M_0P_0A$ is established, and thus $M_0P_1+(1-P_1)M_0P_0A$ pieces of the trap regions $Y_1$ exist. It is to be noted that the A and a will be described later. In this case, the trap number Mt in the passage of time T is $M_t=M_0P_0A$. Consequently, the number of the trap occurring regions $Y_1$ together with the last X-ray irradiation is $Y_1=M_0P_1+(1-P_1)M_0P_0A$ in total.

As a result, at the point of completing the second X-ray irradiation, the number of electrons blocked with the electron trap is $X_1\{Y_1/N\}$ and the electron number $Z_1$ output from the detection film is $X_1\{1-Y_1/N\}$.

Next, the third and henceforth X-ray irradiation is executed and the X-ray irradiation is executed i times in total. FIG. 6 shows the relation between the electron number occurred in each pixel, a trap occurring probability, the trap number, the electron number to be output and the sensitivity of the detector in the embodiment formed from the foregoing theory. As it is clear from the FIG. 6, supposing the electron number occurred at a predetermined time t is $X_i$, and the trap occurring probability in accordance with $X_i$ is $P_i$, the trap number $Y_i$ can be expressed in $Y_i=M_0P_i+(1-P_i)Y_{i-1}A$. Further, the trap number $Y_i=M_0P_i+(1-P_i)Y_{i-1}A$ described in FIG. 6 is a regression type operation.

In the trap number $Y_i=M_0P_i+(1-P_i)Y_{i-1}A$, $P_i$ is predetermined as a correction condition as described above and stored in the memory 56. Therefore, in order to estimate the number of the trap quantitatively, it is necessary to determine the maximum number $M_0$ of the trap possible range, and parameters A and a. These can be determined as follows, for example.

That is, firstly, the relatively strong X-ray is continuously irradiated with a constant intensity from the X-ray tube lamp 11 to the X-ray solid plane detector 37 in the state where there is no subject to be analyzed. The electron number $X_i$ occurred in one pixel can be estimated form the exposure conditions (the tube voltage, the tube current and the like) at this point and the foregoing collection condition.

However, the electron number $Z_i$ to be output is not $X_i$ but $Z_i=X_i(1-Y_i/N)$ due to the electron trap, $Y_i$ can be obtained from $Y_i=N(1-Z_i/X_i)$ from $Z_i$, $X_i$ and N when it is supposed that N=1000. It is to be noted that $Z_i$ can be calculated from the output of the X-ray detector. And, N may be determined considering a necessary accuracy, complexity and the like. If N is set to a large value, more accurate correction can be performed although the complexity increases.

Figure 9:
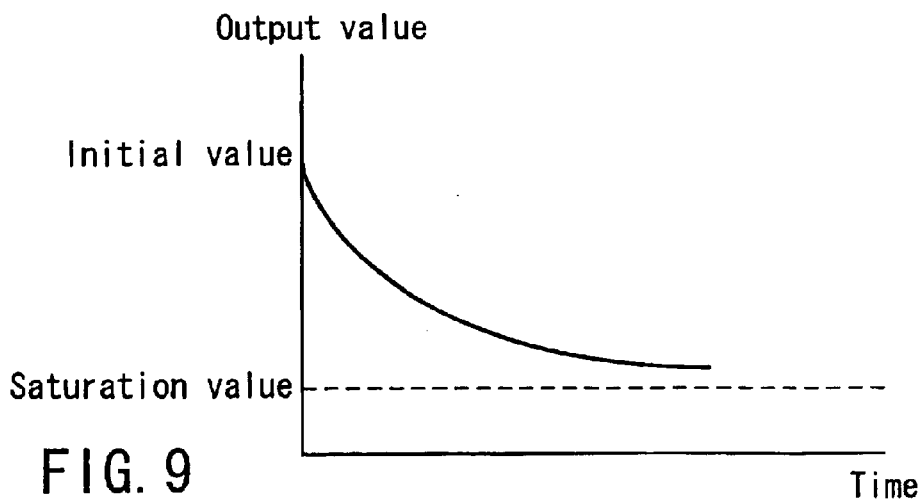
FIG. 9 is a graph regarding the relation between the X-ray exposure time and output.

Furthermore, when the X-ray exposure continues, a lower limit saturation state appears in the electron number to be output at a constant value, that is, the output value of the detector. This shows the case where the electron traps have occurred in the maximum number, and shows the state where $P_i$ substantially becomes 1. FIG. 9 shows the graph regarding the relation between the time and output value when the X-ray is continuously irradiated.

In this state, since the trap number $Y_s$ is $Y_s=M_0$ rather than $P_i=1$, $M_0=Y_s=N(1-Z_s/X_s)$ is established, and $M_0$ can be calculated when N is a proper value, for example, N=1000. It is to be noted that $Z_s$ is the electron number output from the detection film under the saturation state.

Figure 10:
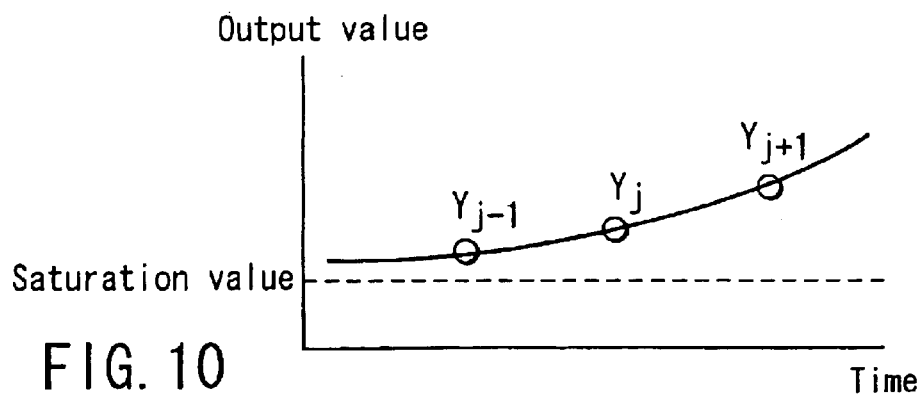
FIG. 10 is a graph regarding the relation between a recovery time and output.

Next, the continuous X-ray exposure is stopped in this state, and the X-ray having the constant intensity is irradiated intermittently with a relatively long interval. The graph as shown in FIG. 10, for example, is obtained when the relation between the time and output value at this point is measured. It is to be noted that white circles displayed intermittently are measured values showing the output during the X-ray exposure, and the solid line shows the interpolation curve.

Herein, consideration is made for three times of irradiation among the irradiation that has been intermittently performed. Supposing the trap numbers in the three times are $Y_{j-1}$, $Y_j$ and $Y_{j+1}$, $Y_j=M_0P_j+(1-P_j)Y_{j-1}\exp(-at_1)$ and $Y_{j+1}=M_0P_{j+1}+(1-P_{j+1})Y_j\exp(-at_2)$ are displayed as in FIG. 6. Since the electron number to be occurred is constant when the X-ray intensity is constant, the trap occurring probability is also constant, that is, $P_j=P_{j+1}$. It is to be noted that t1 shows an X-ray irradiation interval time between the first time and the second time, that is, j−1 and j, and t2 shows the X-ray irradiation interval time between the second time and the third time, that is, j and j+1.

Each of the trap numbers $Y_{j-1}$ to $Y_{j+1}$ can be obtained from the electron numbers $Z_{j-1}$ to $Z_{j+1}$ to be output as described above, a can be obtained from the two expressions: $Y_j=M_0P_j+(1-P_j)Y_{j-1}\exp(-at_1)$ and $Y_{j+1}=M_0P_{j+1}+(1-P_{j+1})Y_j\exp(-at_2)$.

Further, although the embodiment has shown the case where $M_0$ and a are measured with one experiment, it is matter of course that $M_0$ and a can be measured independently. Particularly regarding a, the X-ray does not need to be irradiated to the saturation value when the degree of recovery can be measured.

Data Correction in the Signal Processing Unit

As described above, the number Zi of the electrons outputted from the detection film is estimated to be Zi=Xi$\{1-Yi/N\}$ from the trap number Yi=$M_0$Pi+(1−Pi) Yi−1A. That is, the signal value outputted from each pixel will be influenced by the coefficient $\{1-Yi/N\}$ by the electronic trap. Therefore, the influence by the electronic trap can be eliminated by the correction which cannels the coefficient, in other words, by integrating $1/\{1-Yi/N\}$ to the output value from each pixel. Thus, in order to remove the influence by the electronic trap, the coefficient integrated from each pixel to the output value is called sensitivity correction coefficient. In the above-mentioned example, the sensitivity correction coefficient is $1/\{1-Yi/N\}$.

As an approach of acquiring this correction by sensitiveness multiplier, there are the approach based on the sensibility characteristic and the approach based on the offset characteristic. The approach based on the sensibility characteristic is the approach of acquiring for the correction by sensitivity correction coefficient directly the number of input electrons, and the number of output electrons influenced of the electronic trap, as described above. On the other hand, the approach based on the offset characteristic is the approach of acquiring the correlation of the offset characteristic and the electronic trap for the correction by sensitivity correction coefficient indirectly.

Hereafter, in this embodiment, the data correction by the approach based on the sensibility characteristic will be explained, referring to FIG. 7 and FIG. 8. In addition, the approach based on the offset characteristic will be explained in the second embodiment.

Figure 7:
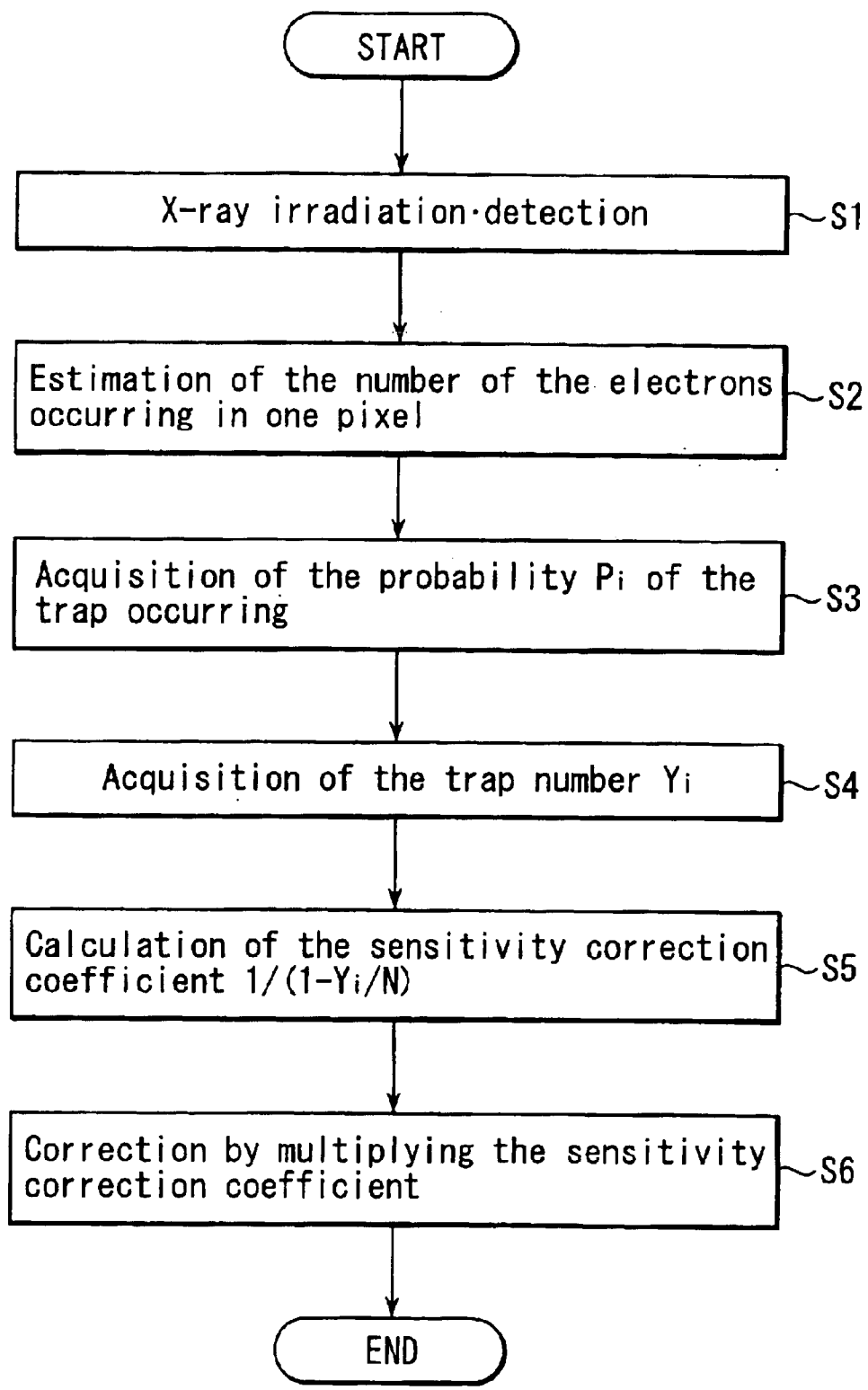
FIG. 7 is a flowchart for explaining the data correction by the approach based on the sensitivity characteristic.

FIG. 7 is a flowchart for explaining the data correction by the approach based on the sensitivity characteristic. In FIG. 7, the X-ray irradiation according to the predetermined sequence is executed first, and the X-ray signal is detected (step S1).

Figure 8:
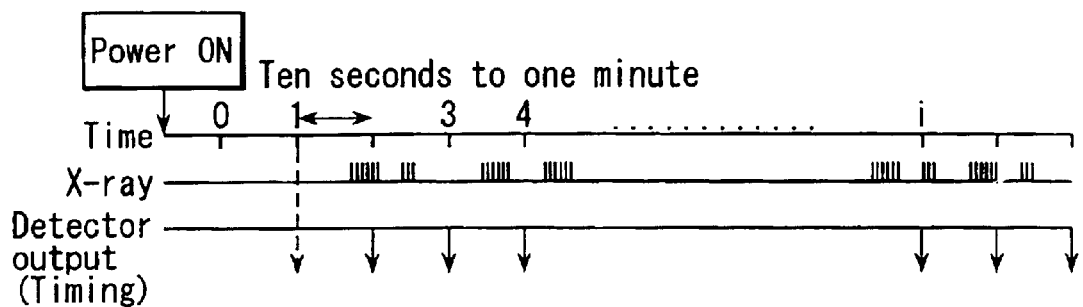
FIG. 8 is a timing chart of the X-ray irradiation and the output of an X-ray solid plane detector.

FIG. 8 is a timing chart of the X-ray irradiation in step S1 and the output of an X-ray solid plane detector. In FIG. 8, the irradiation of X-ray is given irregularly and this drawing shows the case where the output of the X-ray solid flat surface detector is not performed synchronizing with X-ray irradiation.

For example, as the output from the X-ray detector, the X-ray applied in a predetermined time interval, for example, an interval of ten seconds to one minute, is output after performing addition or average. It is to be noted that a method of obtaining the output after performing addition or average is realized by controlling the gate driver 45 and the initial step integrating amplifier 71.

The data correction unit 21a estimates the electron number $X_i$ occurred in one pixel of the detection film 22 from the signal output from the ADC 65 and a collection condition stored in the memory 56 (step S2).

Herein, the estimation of $X_i$ when imaging the subject to be analyzed is not performed form the exposure condition of the X-ray as in the case where there is no subject to be analyzed, but sets a number, in which the electron number Zi output form the detection film is multiplied with an inverse number of the sensitivity correction coefficient $1/(1-Y_{i-1}/N)$ in a previous data, as a reference. Specifically, the electron number $X_i$ occurred is presumed as $Z_i(1-Y_i/N)$.

This is because, unlike the case where there is no subject to be analyzed, the X-ray is absorbed in the body of the subject to be analyzed in the case where there is the subject to be analyzed, and thus it is difficult to know the quantity of the X-ray that reaches the X-ray detector.

Next, the X-P conversion unit 52 obtains the trap occurring probability $P_i$ corresponding to the estimated electron number $X_i$ by using a look-up table stored in the memory 56 (step S3). If the look-up table does not have a value equal to $X_i$ in this case, the value closest to $X_i$ may be approximated on the look-up table to obtain Pi, or Pi may be obtained from previous/subsequent values by performing linear interpolation. It is to be noted that the look-up table will be described later.

Next, the trap number calculation unit 53 obtains a current trap number Yi by performing regression type operation that is $Y_i=M_0P_i+(1-P_i)Y_{i-1}A$ as described above (step S4). It is to be noted that the operation uses the parameters $M_0$ and a stored in the memory 56 and $Y_{i-1}$ already calculated at the previous sampling.

Next, the sensitivity correction coefficient calculation unit 54 calculates the sensitivity correction coefficient as in $1/(1-Y_i/N)$ as described above (step S5). The calculation method of the sensitivity correction coefficient follows described above.

Finally, the multiplier 55 multiplies the sensitivity correction coefficient with the original X-ray detector, and thus the sensitivity is corrected step S6).

After this, the data signal corrected with sensitivity is converted to the image display signal in image display signal conversion unit 21b. The CRT 25 displays the X-ray image based on the inputted display signal.

Example of Formation of LUT

The LUT which is beforehand stored in the memory 56 and is used for the data correction processing described above will be explained in detail. The look-up table used for the data correction processing is the concretely one in which the relation between $X_i$ and $P_i$ is described and formed as following.

Firstly, similarly to the case of obtaining $M_0$, the electron number $X_i$ occurred in one pixel is estimated from the X-ray exposure condition and the like.

$Y_i=M_0P_i+(1-P_i)Y_{i-1}A$ is established regarding the trap number $Y_i$, but a trapped state disappears in the state where time has passed and the sensitivity has recovered, that is, the trap number can be made $Y_{i-1}=0$ and thus $Y_i=M_0P_i$. Therefore, $P_i=Y_i/M_0$ is established from $M_0$ already obtained and $Z_i$ obtained from an actual output value, and thus $P_i$ can be obtained.

Accordingly, the intensity of the X-ray is changed in the state where every time the sensitivity recovers, and the output of the X-ray detector is measured for a plural times, and the relation of the electron number $X_i$ and the trap occurring probability $P_i$ can be obtained. The look-up table is the one in which the relation is stored.

The foregoing is the information stored in the memory 56 prior to the imaging or the like of the subject to be analyzed, and the imaging or the like of the subject to be analyzed is performed using the information. It is to be noted that an operator himself/herself may obtain the information stored here, or the information may be previously saved in a storage medium such as a hard disc, a CD-R and a DVD before the shipment of the apparatus. More accurate correction can be performed if an inspection is regularly performed to update the stored information.

Variations

Next, a first variation example in the first embodiment will be described. In the first embodiment, the characteristic of the detection film 22 is described in the case where the trap number simply reduces with time. On the contrary, the variation example is a model in which the trapped electrons are discharged in the process of the phenomenon. The model in which the trapped electrons are discharged with time can be considered as a model where the increase of the offset is taken in consideration.

In the variation example, the electrons discharged from the detection film 22 should be a component proportional to the trap number.

In other words, the electron number discharged from one pixel of the detection film is added with the electron number $BY_{i-1}$, which is proportional to the trap number $Y_{i-1}$ of a previous time, and the sensitivity is calculated as $X_i(1-Y_i/N)+BY_{i-1}$. It is to be noted that $B \geq 0$ is established.

The method of obtaining B uses the state where the sensitivity of the detector is saturated, which is used in the first embodiment. More specifically, similarly to the first embodiment, the X-ray is continuously irradiated and the electron number Zi output from the detector is obtained, as shown in FIG. 8. The $Z_i$ can be: $Z_i=X_i(1-Y_i/N)+BY_{i-1}$, and $Z_i=X_i(1-M_0/N)+BM_0$ because $Y_i \square Y_{i-1}$ and $Y_{i-1}=M_0$.

Next, the exposure of the X-ray is stopped in the state where the sensitivity of the detector is saturated. Then, the electron does not occur in the detection film to which the X-ray is not irradiated, that is, Xi=0 is obtained. At this point, the detector outputs the electrons by only the quantity of the offset, and the electron number Z'i can be $M_0B$. Specifically, $Z'i=M_0B$.

Therefore, $M_0=N\{1-(Zi-Z'i)/Xi\}$ is established when this is assigned to the foregoing $Zi=Xi(1-M_0/N)+BM_0$., and thus $M_0$ can be obtained and B can be obtained from $B=Z'i/M_0$.

The obtained B is stored in the memory 56 similarly to the first embodiment and used.

The variation example is the case where the trapped electrons are discharged with time, and more accurate correction can be performed by taking in consideration the increase of the offset.

Many kinds of variation examples can be considered other than this variation example. For example, it is possible to consider a model in which the discharged electron number not proportional to the trap number but proportional to the change of the trap number, that is, $Z_i=X_i(1-Y_i/N)+B'(Y_{i-1}-Y_i)$. In selecting the model, a proper model may be specified by an experiment, or may be determine considering the amount of calculations and the complexity of a circuit.

For example, comparing the first embodiment with the variation example, it is considered that the variation example has more amounts of calculations due to the use of B, but it can perform the correction where the offset is considered.

Further, among the models, the one such as the first embodiment and the variation example that performs the sensitivity correction or the offset correction based on the output of the regression type operation has a very wide range of applications, and the deterioration of the sensitivity and the offset can be corrected with simple circuit.

Still further, in the first embodiment and the variation example, the trap number of the initial state is set to 0, that is, $Y_0=M_0P_0$, but other than this, it may be set to the value of the last $Y'_i$ that was performed before.

However, the value of $Y'_i$ should be changed a little based on a passage of time T between the time when the operation was performed before and the current time.

This change is possible if the characteristic of the detection film is measured in advance and the measurement is performed as to how the trap number changes corresponding to an electrical conduction state.

For example, if it is found out that the trap number naturally reduced by 1% per one hour through the measurement, the operation can be started setting the initial value of the trap number as $Y_0=M_0P_0+\exp(-0.01_t)Y'_i$ because the reduction of the trap number by $\exp(-0.01T)$ is estimated in the passage of time T (hour).

It is to be noted that description was made particularly for the one generally called an X-ray plane detector among the X-ray detectors, but the arrangement of the detection devices are not particularly limited.

Further, although the first embodiment and the variation example show the case where the X-ray exposure and the detector output are not synchronized, they may be synchronized.

Furthermore, the characteristic of the detection film is shown in the two cases of the first embodiment and the variation example, but the characteristic of the detection film is not particularly limited. There are cases where the foregoing model is effectively used when the characteristic of the detection film is changed a little.

Still further, although each embodiment and the variation example show the case where hardware performs the sensitivity correction, all or a part of the correction may be performed on the hardware.

Next, the advantage acquired by the X-ray diagnostic apparatus 1 with the configuration described above will be explained by giving some examples.

Firstly, the advantage in the case where an abdomen is fluorographed after a cervix has been imaged is explained.

Figure 11:
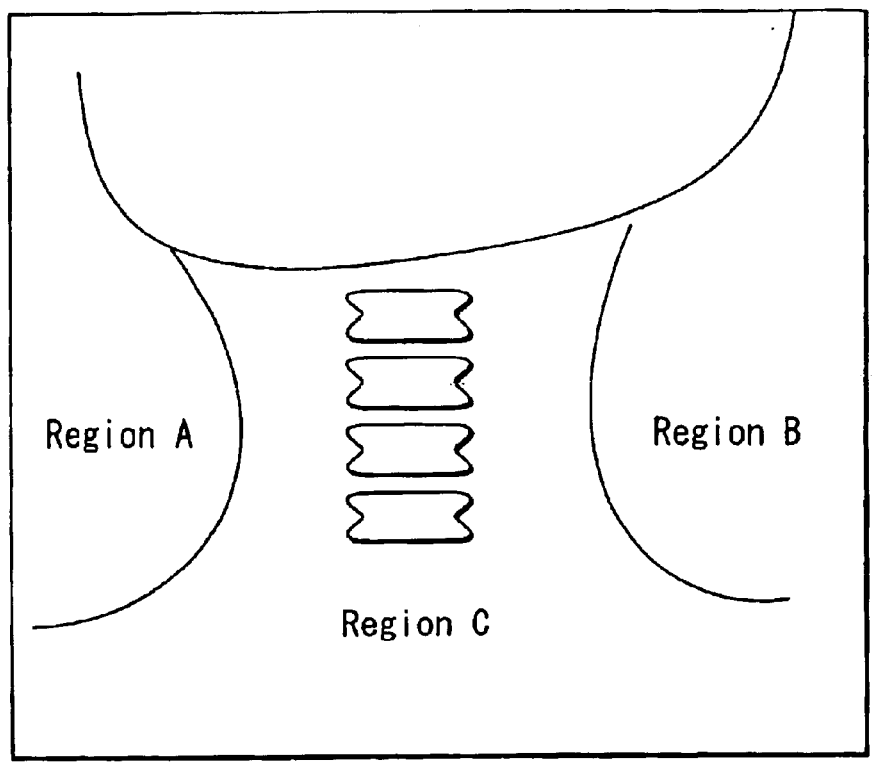
FIG. 11 is drawing for explaining the effectiveness of the X-ray diagnostic apparatus according to the present embodiment.

In the conventional X-ray diagnostic apparatus, strong X-ray is irradiated to image a cervix shown in FIG. 11. In this case, Regions A and B are the regions where the X-ray is made incident directly to the detector without passing a subject to be analyzed. Therefore, comparing to a region C to which the X-ray is made incident passing through the subject to be analyzed, the stronger X-ray is irradiated in the regions A and B. As a result, the sensitivity temporarily reduces and the offset increases in the regions A and B comparing to the region C.

Figure 12:
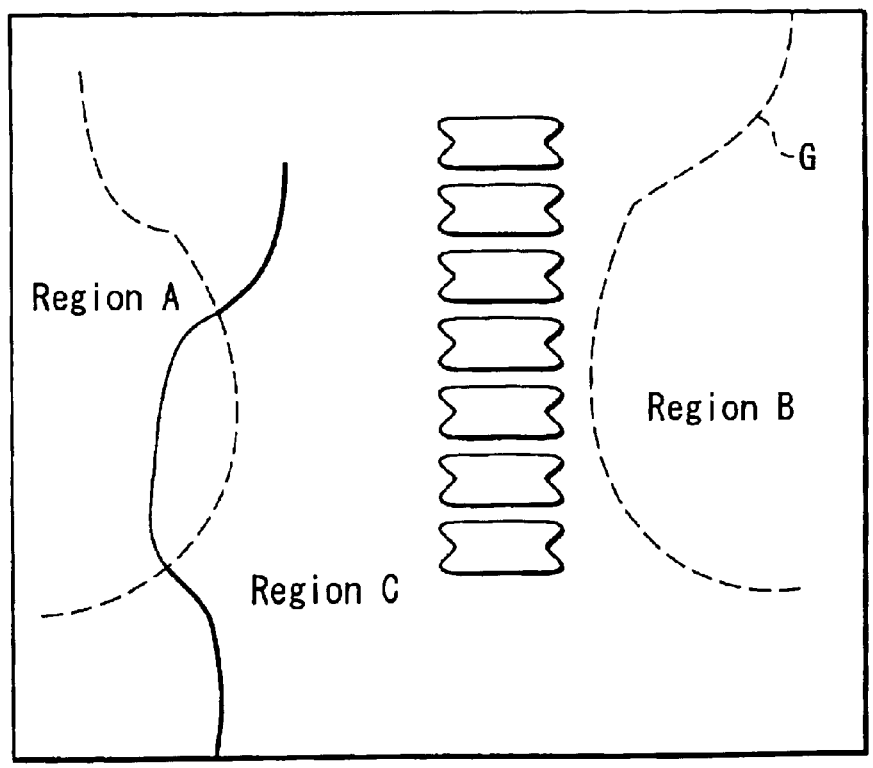
FIG. 12 is drawing for explaining the effectiveness of the X-ray diagnostic apparatus according to the present embodiment.

If weak X-ray is irradiated to acquire the fluorography of the abdomen shown in FIG. 11 after the fall of such sensibility and the increase in the offset have occurred, as shown in FIG. 12, the last photography image may be overlapped on the perspective diagram image as a ghost G. Especially this is because each of the pixel which exists in Ranges A and B is influenced by the signal detected by the last imaging.

On the other hand, in this X-ray diagnostic apparatus 1, since the data correction which removes the influence of the signal detected last time is performed to the output value of each pixel, the ghost G as shows in FIG. 12 can be removed.

Next, the advantage acquired in the case where prolonged fluorography is executed is explained.

Since the fluorography uses the relatively light X-ray, a contrast difference is smaller than the imaging. Accordingly, images having the different luminance are formed in the regions A and C or the regions B and C as shown in FIG. 12 for example, the fluorography receives great influence from the reduction of the sensitivity or the increase of the offset by imaging, and thus there is a case where an appropriate image cannot be displayed. It is to be noted that this example shows the case where a catheter (shown in a solid line) that may be used in the fluorography is inserted in the subject to be analyzed. Further, the example shows the case where the catheter exists across the regions A and C, and the region A of the catheter is displayed darker than the region C.

Also in this case, in the X-ray diagnostic apparatus 1, since the data correction which removes the influence of the signal detected last time is performed to the output value of each pixel, change of brightness as shown in FIG. 12 can be removed.

Furthermore, not only when the fluorography and the imaging are continuously performed but also when the imaging is performed by using a collimator for example, the sensitivity in the region where the X-ray is blocked by the collimator on the X-ray detector and the sensitivity in the region where the X-ray is not blocked are remarkably different, and thus the appropriate image cannot be displayed as described above when the collimator is replaced.

In addition, in the case other than the case where the fluorography and the imaging are continuously performed or where the collimator is replaced, similar problem may possibly occur because the transmittance of the X-ray through muscle, bone and the like is different only when an imaging position changes.

As described above in detail, according to the X-ray diagnostic apparatus, at least one of the sensitivity of the detector and the offset can be corrected taking into consideration a temporal change, and the measurement can be performed by reducing the influence of the dispersion of the detector sensitivity. Therefore, the acceptable image can be provided.

In addition, in the case where the sensitivity of the detector is changed in time, the acceptable image can be provided by executing this correction according to the sensitivity.

Second Embodiment

In the second embodiment, the X-ray diagnostic apparatus which acquires the sensitivity correction coefficient based on the correlation relation with the offset characteristic to correct a data, will be described. Note that, in the following explanation, the correction for removing the ghost image generated by the electronic trap is called "ghost correction."

Figure 13:
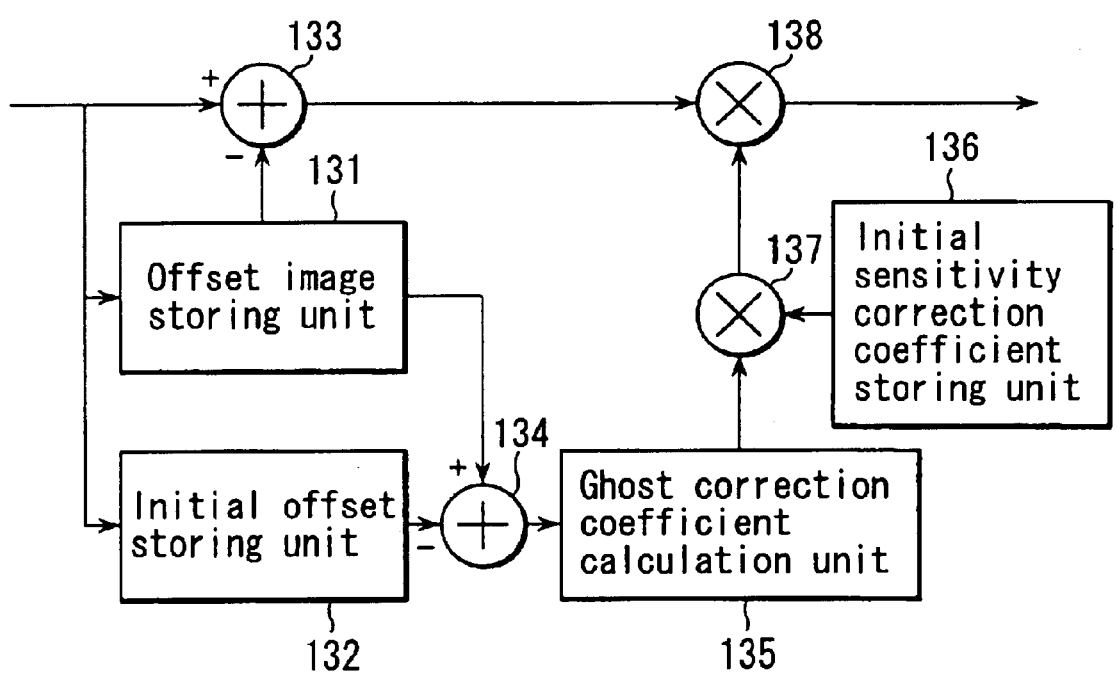
FIG. 13 is a block diagram of a data correction unit 21a according to a second embodiment.

FIG. 13 is a block diagram of the data correction unit 21a according to the second embodiment. As shown in FIG. 13, the data correction unit 21a comprises: a offset image storing unit 131, an initial offset storing unit 132, a subtraction unit 133, a subtraction unit 134, a ghost correction coefficient calculation unit 135, an initial sensitivity correction coefficient storing unit 136, a multiplier 137 and a multiplier 138.

The offset image storing unit 131 stores the offset image (hereinafter, referred to as a first offset image) data just before a X-ray irradiation. Here the offset image is the image which the X-ray flat surface detector 37 detects without an X-ray irradiation. That is, the offset image is an image based on the background electronic signal which is caused by the dark current which each pixel has in the X-ray flat surface detector 37, the offset which each integral amplifier has the undercurrent X-ray from the X-ray generating system and is detected in the condition that X-ray are not irradiated. In this offset image, the increment of the offset component produced by a previous X-ray irradiation is included.

The initial offset storing unit 132 stores the offset image in which the increment of the offset component produced by a previous X-ray irradiation is not included (hereinafter, referred to as a second offset image) data.

The first subtraction unit 133 executes an offset correction by subtracting offset image data stored in the offset image storing unit 131 just before a X-ray irradiation from X-ray image data output form the ADC 65.

The second subtraction unit 133 acquires the difference between images by subtracting a first offset image from a second offset image. The difference is the increment of the offset component produced by a previous X-ray irradiation.

The ghost correction coefficient calculation unit 135 stores sensitivity correction coefficients which are acquired according to the correlation relation between the predetermined increment of offset component and the sensitivity decrease (hereinafter, referred to as first sensitivity correction coefficients) Concretely, the ghost correction coefficient calculation unit 135 is LUT (Look Up Table), for example. Referring to the stored the correlation relation between the predetermined increment of offset component and the sensitivity decrease, the ghost correction coefficient calculation unit 135 calculates the first sensitivity correction coefficient by which the sensitivity decrease is corrected based on the input increment of offset component, and outputs the first sensitivity correction coefficient.

The initial sensitivity correction coefficient storing unit 136 stores sensitivity correction coefficients which is in the condition of not including the sensitivity decrease of a X-ray irradiation (hereinafter, referred to as second sensitivity correction coefficients). The sensitivity change not owing to a X-ray irradiation can be corrected by multiplying the second sensitivity correction coefficient by the X-ray imaging data.

The first multiplier 137 multiplies the first sensitivity correction coefficient from the ghost correction coefficient calculation unit 135 by the second sensitivity correction coefficient from the initial sensitivity correction coefficient storing unit 136.

The second multiplier multiplies the X-ray imaging data input from the first subtraction unit 133 by the value of the product of the second sensitivity correction coefficient and the second sensitivity correction coefficient input from the first multiplier 137.

Next, the data correction processing which is executed by the data correction unit 21a with the above configuration will be described.

Firstly, in the first subtraction unit 133, the offset correction is executed to the X-ray image data output from the ADC 65 based on the offset image data which is acquired just before the X-ray irradiation and stored in the offset image storing unit 131.

Next, in the second multiplier, the initial sensitivity correction and the ghost correction are executed by multiplying the value of the product of the second sensitivity correction coefficient and the second sensitivity correction coefficient input from the first multiplier 137.

The X-ray image data corrected by the second multiplier 138 is converted to the signal for displaying the image and displayed on the CRT 25.

With this configuration, the same effectiveness as the first embodiment can be acquired.

It is note that the variation described in the first embodiment is applicable to the X-ray diagnostic apparatus according to the second embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus, comprising:
   an X-ray source which exposes an X-ray;
   a detector configured to detect an incident X-ray from said X-ray source and to generate a signal;
   a memory which stores a table in which degrees of signal decay are acquired at every intensity of an X-ray;
   an estimation unit configured to estimate a degree of decay of a first signal generated previously by said detector in response to a last X-ray exposure by said X-ray source based on the table; and
   a first correction device configured to correct a value of a second signal generated by said detector subsequent to the generation of the first signal, based on the degree of the decay of the first signal.

2. The X-ray diagnostic apparatus according to claim 1, wherein said X-ray detector is an X-ray detector that utilizes a semiconductor in an X-ray detection portion.

3. The X-ray diagnostic apparatus according to claim 2, wherein said X-ray detector is a direct conversion type detector.

4. The X-ray diagnostic apparatus according to claim 3, wherein said X-ray detector includes selenium.

5. The X-ray diagnostic apparatus according to claim 1, further comprising:
   a second correction device configured to correct the value of the first signal based on a time from the last time of an X-ray exposure by said X-ray source.

6. The X-ray diagnostic apparatus according to claim 1, wherein the degree of decay of signals in the table is acquired based on a number of input electrons from said X-ray to said detector and a number of output electrons influenced by an electric trap from said detector to said estimation unit.

7. The X-ray diagnostic apparatus according to claim 1, wherein the degree of decay of signals in the table is acquired based on a correlation of an offset characteristic and electric trap.

8. An X-ray diagnostic apparatus, comprising:
   an X-ray source which exposes an X-ray;
   an X-ray detector having a plurality of semiconductor elements which are arranged in a shape of a two-dimensional matrix to detect an incident X-ray and generate signals;
   a memory that stores a table in which degrees of signal decay are acquired at every intensity of an X-ray;
   an estimation unit configured to estimate a degree of decay of first signals generated previously by the plurality of semiconductor elements in response to a last X-ray exposure by said X-ray source, based on the table; and a first correction device configured to correct a value of second signals generated by the plurality of semiconductor elements subsequent to the generation of the first signals, based on the degree of the decay of the first signals.

9. The X-ray diagnostic apparatus according to claim 8, wherein said semiconductor elements are direct conversion type elements.

10. The X-ray diagnostic apparatus according to claim 8, wherein each of the semiconductor elements includes detection film utilizing selenium.

11. The X-ray diagnostic apparatus according to claim 8, further comprising:

a second correction device configured to correct each of the values of the first signals based on a time from the last time of an X-ray exposure by said X-ray source.

12. The X-ray diagnostic apparatus according to claim 8, wherein the degree of decay of signals in the table is acquired based on a number of input electrons from said X-ray to said detector and a number of output electrons influenced by an electric trap from said detector to said estimation unit.

13. The X-ray diagnostic apparatus according to claim 8, wherein the degree of decay of signals in the table is acquired based on a correlation of an offset characteristic and electric trap.

14. An X-ray diagnostic apparatus, comprising:

a X-ray detector having a plurality of semiconductor elements arranged in the shape of a 2-dimensional matrix and configured to detect an incident X-ray and generate electric information;

a memory configured to store a correlation relation between an offset characteristic and a sensitivity characteristic of each of the semiconductor elements;

a first estimation unit configured to estimate an offset characteristic change of each of said semiconductor elements based on a value of a signal previously detected by each of said plurality of the semiconductor elements at least last time;

a second estimation unit configured to estimate a sensitivity characteristic change of each of said semiconductor elements from the estimated offset characteristic change according to the correlation relation; and a correction device configured to execute a correction by which each of the sensitivity characteristic change is cancelled to each of the signals output from each of said plurality of the semiconductor elements.

15. The X-ray diagnostic apparatus according to claim 14, wherein said semiconductor elements are direct conversion type elements.

16. The X-ray diagnostic apparatus according to claim 14, wherein each of the semiconductor elements includes detection film utilizing selenium.

17. The X-ray diagnostic apparatus according to claim 14, further comprising: a second correction device configured to correct each of the value of the signal previously detected by each of the semiconductor elements at least last time based on a passage of time from a time of the last signal value detection by each of the semiconductor elements.

* * * * *